US00PP12901P2

(12) United States Plant Patent
Noodelijk

(10) Patent No.: US PP12,901 P2
(45) Date of Patent: Sep. 3, 2002

(54) CHRYSANTHEMUM NAMED 'CUPIDORES'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/562,277

(22) Filed: May 1, 2000

(51) Int. Cl.[7] ..... A01H 5/00
(52) U.S. Cl. ..... Plt./291
(58) Field of Search ..... Plt./291, 286, 287

(56) References Cited

PUBLICATIONS

UPOV–ROM GTITM Computer Database 2001/01, Feb. 6, 2001, GTI Jouve Retrieval Software, Citation for Dendranthema 'Cupido'.*

* cited by examiner

*Primary Examiner*—Bruce R. Campell
*Assistant Examiner*—June Hwu

(57) ABSTRACT

A chrysanthemum plant named 'CUPIDORES' characterized by its large sized blooms with pink ray florets and prolific branching; natural season flower date August 28–31; blooming for a period of 6 weeks.

2 Drawing Sheets

BACKGROUND OF THE INVENTION

'CUPIDORES' is a product of a breeding and selection program for outdoor pot mums (garden mums) which had the objective of creating new chrysanthemum cultivars with a decorative type flower, a natural season flower date around August 28–31; blooming for a period of 6 weeks. The new plant of the present invention comprises a new and distinct cultivar of Chrysanthemum plant. 'CUPIDORES' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in August 1996. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
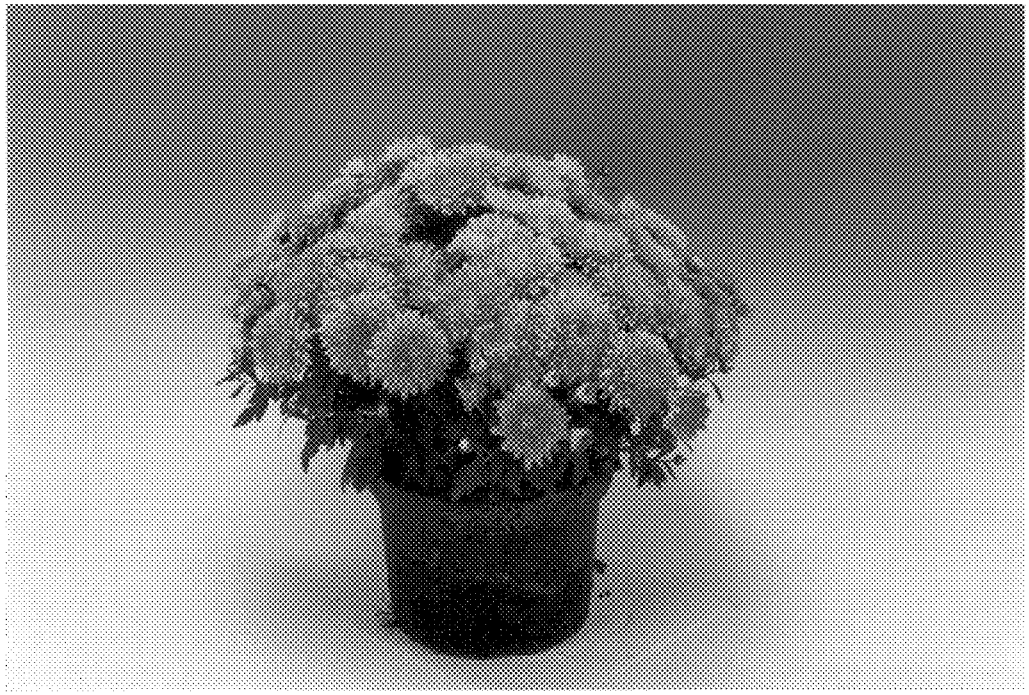
FIG. 1 shows a plant of the cultivar in full bloom.
Figure 2:
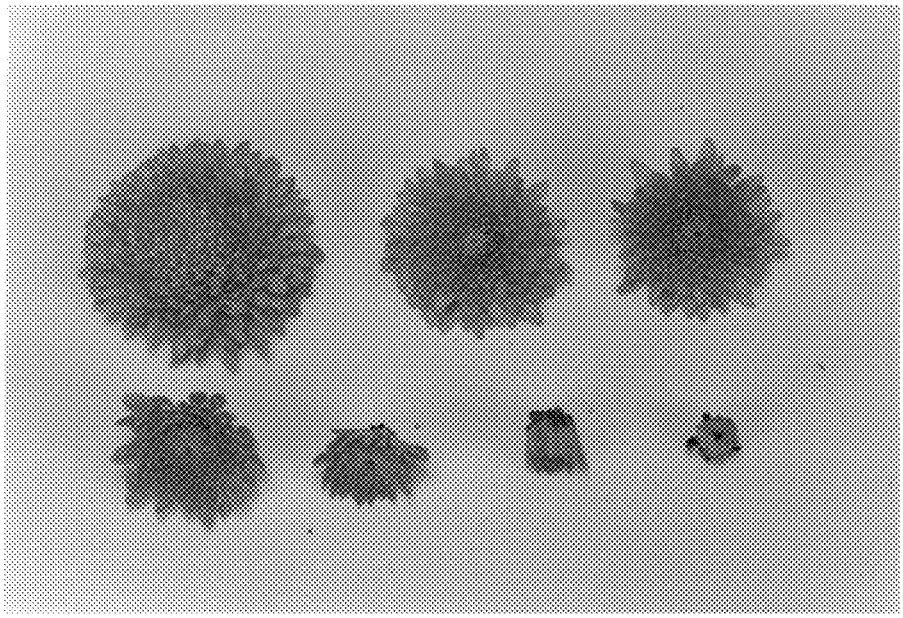
FIG. 2 shows the various stages of bloom of the new cultivar.
Figure 3:
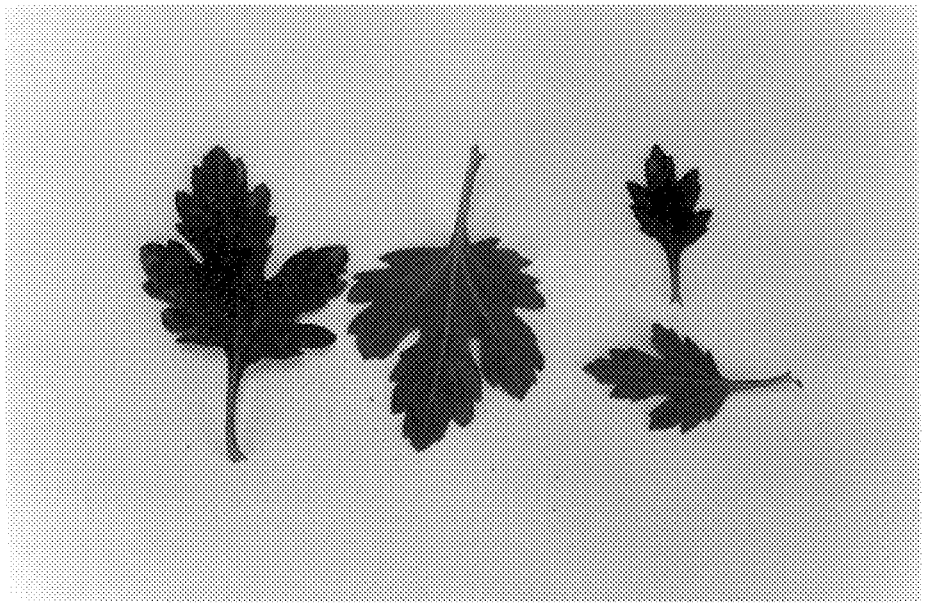
FIG. 3 shows the various stages of foliage and petiole of the new cultivar.

This new variety of chrysanthemum is of the botanical classification *Dendranthema grandiflora*. The observations and measurements were gathered from plants grown out door in Rijsenhout, Holland under natural day length and temperature and planted week 22 in 1997 and 1998. The natural blooming date of this crop was August 28–31 (week 35). The average height of the plants was 24–26 cms. No growth retardants were used. This new variety produces LARGE sized blooms with PINK ray florets and a pink center blooming for a period of 6 weeks.

From the cultivars known to inventor the most similar existing cultivar in comparison to 'CUPIDORES' are 'DEBONAIR' (U.S. Plant Pat. No. 5,324) and 'SYMPHONY' (U.S. Plant Pat. No. 8,782). 'DEBONAIR', 'SYMPHONY' and 'CUPIDORES' have a flower that looks similar. When 'DEBONAIR', 'SYMPHONY' and 'CUPIDORES' are being compared the following differences are noticed: The differences of 'DEBONAIR', 'SYMPHONY' and 'CUPIDORES' are (1) Flower size and color. The flowers of 'CUPIDORES' are larger. The flower color of 'CUPIDORES' is not so dark. (2) Response time. 'CUPIDORES' flowers end of August, 'DEBONAIR' and 'SYMPHONY' after mid September. (3) Vigour. 'CUPIDORES' is less vigorous than 'DEBONAIR' and 'SYMPHONY'.

The following is a description of the plant and characteristics that distinguish 'CUPIDORES' as a new and distinct variety.

The color designations are taken from the plant itself. Accordingly, any discrepancies between the color designations and the colors depicted in the photographs are due to photographic tolerances. The color chart used in this description is: The Royal Horticultural Society color chart, edition 1995.

Botanical Description of CULTIVAR 'CUPIDORES'

Bud:

*Size.*—Large; cross-section 1.6 cm, length 1.5 cm.
*Outside color.*—Greyed-purple 186 C.
*Involucral bracts.*—2 rows, length 7 mm, width 3 mm.
*Involucral bracts among disc-florets.*—Not present.
*Involucral bracts color.*—Green 138 A.

Bloom:

*Type.*—Decorative.
*Height.*—High, 3.5 cm.
*Size.*—LARGE.
*Fully expanded.*—6.0–6.5 cm.
*Number of blooms per branch.*—(Approx. 4–5 blooms per branch).
*Performance on the plant.*—6 weeks.
*Seeds.*—Not produced.
*Fragrance.*—Typical chrysanthemum.

Color:

*Center of the flower* (*disc-florets*).—Immature red 57 C with a small dot of green 151A. Mature red 57 C.

*Color of upper surface of the ray-florets.*—Red 57 C.

*Color of the lower surface of the ray-florets.*—Red-purple 63 D.

*Tonality from distance.*—A gardenmum with large pink decorative flowers.

*Discoloration to color.*—To red-purple 63 C.

Ray florets:

*Texture.*—Upper and under side smooth.

*Number.*—220–240.

*Cross-section.*—Convex.

*Longitudinal axis of majority.*—Incurved, outer rows reflexing.

*Length of corolla tube.*—Medium.

*Ray-floret margin.*—Entire.

*Ray-floret length.*—3.0–3.3 cm.

*Ray-floret width.*—0.4–0.6 cm.

*Ratio length/width.*—High (ray-floret long and narrow).

*Shape of tip.*—Pointed.

*Disc florets.*—None.

*Receptacle shape.*—Domed raised.

Reproductive organs:

*Stamen* (*disc florets*).—None.

*Pollen.*—None.

*Styles.*—Thin.

*Style color.*—Yellow-green 151 C.

*Style length.*—4 mm.

*Stigmas.*—Yellow-green 151 C.

*Stigma width.*—1 mm.

*Ovaries.*—Enclosed in calyx.

Plant:

*Form.*—A garden mum meant for out-door use.

*Growth habit.*—Spreading.

*Growth rate.*—Slow.

*Height.*—24–26 cm.

*Width.*—26–28 cm.

*Stem color.*—Green 138 A.

*Stem strength.*—Weak.

*Stem brittleness.*—Present.

*Stem anthocyanin coloration.*—Absent.

*Length of lateral branch.*—From top to bottom 10–11 cm.

*Lateral branch color.*—Green 138 A.

*Lateral branch, attachment.*—Weak.

*Branching* (*average number of lateral branches*).—Prolific with 6–7 breaks after pinching.

*Peduncle length.*—1.5–2.0 cm.

*Peduncle color.*—Green 138 A.

*Natural season blooming date.*—August 28–31.

Foliage:

*Color.*—Upper side green 137 A. Under side green 137 C.

*Size.*—Small; length 5.0–5.5 cm, width 4.5 cm.

*Quantity* (*number per lateral branch*).—10–12.

*Shape.*—Ovate, round.

*Texture upper side.*—Glabrous.

*Texture under side.*—Pubescent.

*Venation arrangement.*—Palmate.

*Shape of the margin.*—Serrated.

*Shape of base of sinus between lateral lobes.*—Round.

*Margin of sinus between lateral lobes.*—Converging.

*Shape of base.*—Truncate sometimes asymmetric.

*Apex.*—Mucronate.

I claim:

1. A new and distinct variety of chrysanthemum plant as described and illustrated.

* * * * *